United States Patent [19]

Lew

[11] Patent Number: 5,005,400

[45] Date of Patent: Apr. 9, 1991

[54] DUAL FREQUENCY DENSITY METER

[76] Inventor: Hyok S. Lew, 7890 Oak St., Arvada, Colo. 80005

[21] Appl. No.: 380,820

[22] Filed: Jul. 18, 1989

[51] Int. Cl.$^5$ .............................................. G01N 9/00
[52] U.S. Cl. ...................................................... 73/32 A
[58] Field of Search ........................................ 73/32 A

[56] References Cited

U.S. PATENT DOCUMENTS 4,679,947  7/1987  Miller et al. ........................ 73/32 A

FOREIGN PATENT DOCUMENTS 554482  6/1977  U.S.S.R. ............................. 73/32 A
1187014  10/1985  U.S.S.R. ............................. 73/32 A
1226173  4/1986  U.S.S.R. ............................. 73/32 A

Primary Examiner—John Chapman

[57] ABSTRACT

An apparatus for measuring density of media moving through a conduit included therein comprises one or two vibrating sections under two different flexural vibrations vibrating at two different natural frequencies which are functions of the stiffness of the vibrating sections of the conduit, density of the media moving therethrough and viscosity of the media as well as the viscosity of the ambient air surrounding the vibrating sections of the conduit. A mathematical combination of the two different natural frequencies of the vibrating section or sections of the conduit eliminates the dependence thereof on the viscosities and determines the density of media accurately independent of the viscosity.

13 Claims, 3 Drawing Sheets

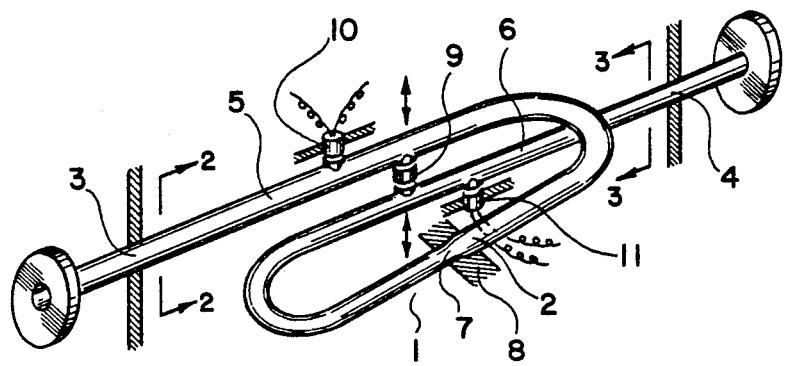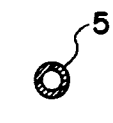
Fig. 1
Fig. 2  Fig. 3
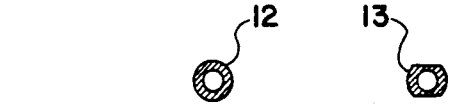
Fig. 5  Fig. 6
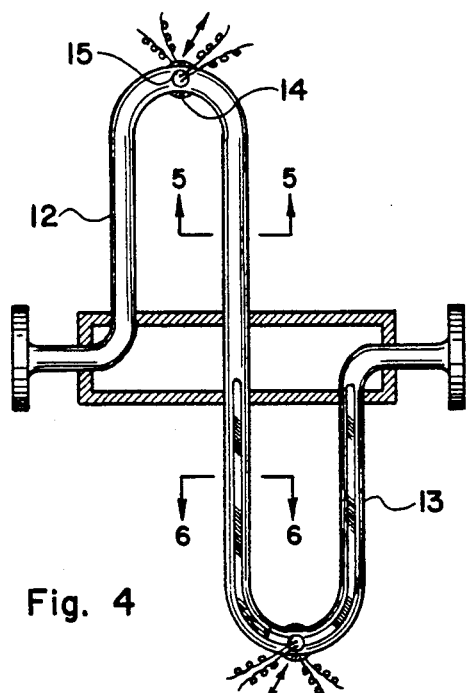
Fig. 4
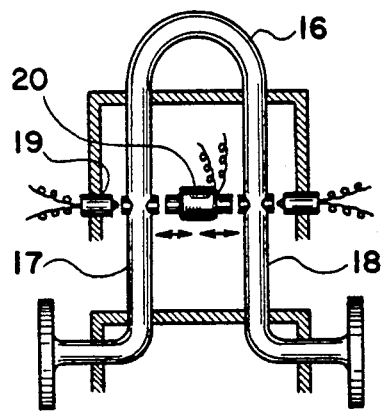
Fig. 7
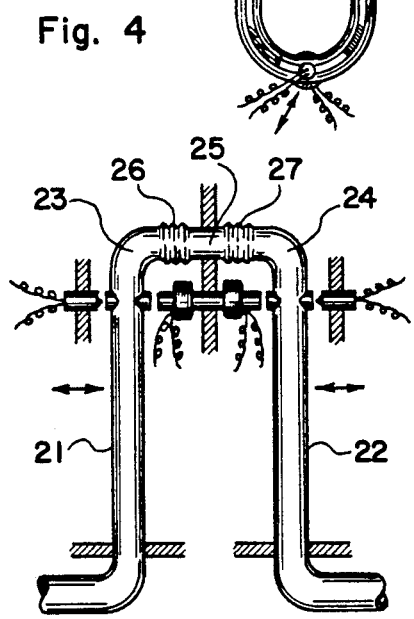
Fig. 8
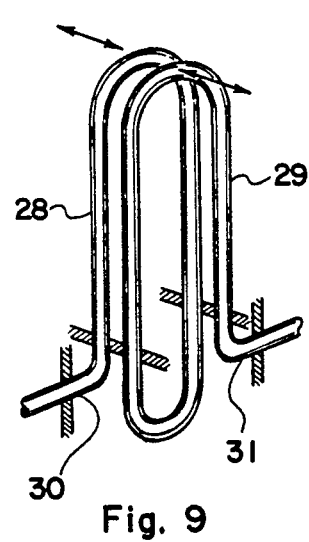
Fig. 9
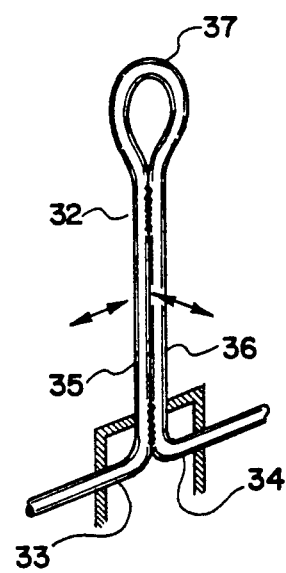
Fig. 10

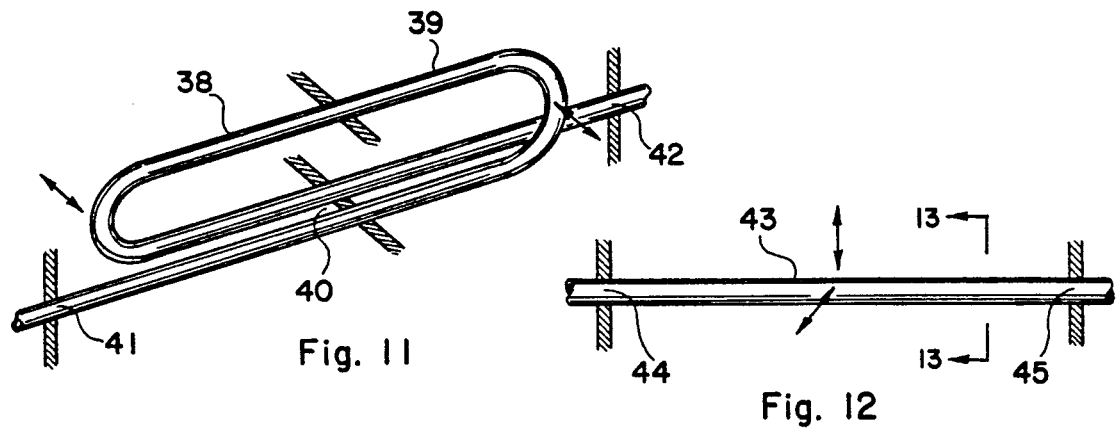
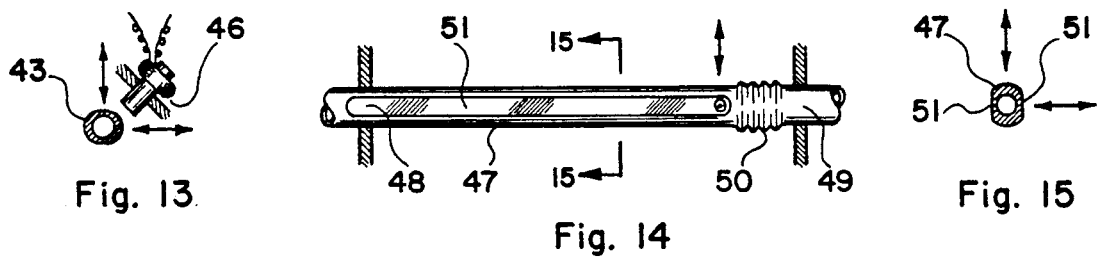
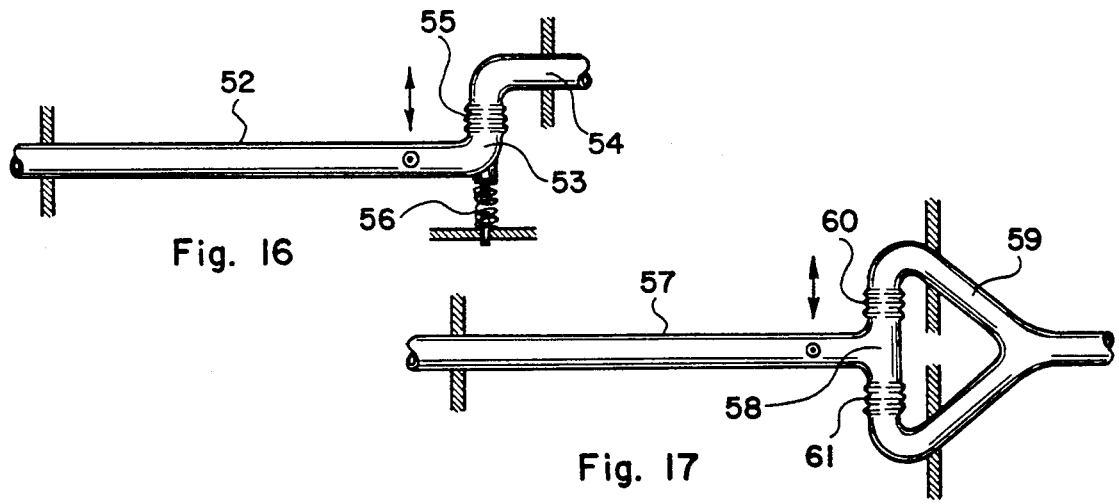
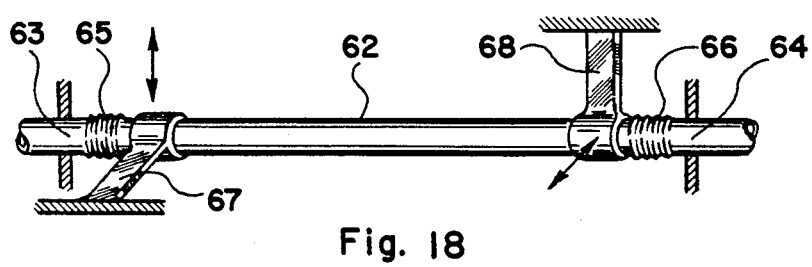

DUAL FREQUENCY DENSITY METER

BACKGROUND OF THE INVENTION

An apparatus measuring density of media comprises a single section of conduit under flexural vibrations in two lateral directions at two different natural frequencies or two sections of conduit under flexural vibrations at two different natural frequencies, wherein the density of the media moving through the conduit is determined from a combination of the two different natural frequencies, in which combination the effect of the viscosity of the media on the natural frequencies is eliminated and, consequently, the density of the media is determined accurately without errors introduced by the effect of the viscosity.

There are many instances in industrial processes and controls handling the flow fluids wherein the density of the moving fluid has to be measured accurately. One particular application of density measurement is to determine the mass flow rate of a fluid medium as a product of the fluid density measured by a density meter and a volume flow rate of the fluid measured by a volumetric flowmeter. There are mass flowmeters available at the present time such as the Coriolis force or convective inertia force mass flowmeters and thermal probe mass flowmeters. These types of mass flowmeters work poorly in measuring flows of highly viscous fluids due to the error in the data acquisition yielding the mass flow rate arising from the effect of the viscosity of the fluid, while they function excellently in the mass flow measurement of low viscosity fluids. One of the more promising approaches to measurement of the mass flow rate is to employ a combination of an accurate density meter and a reliable positive displacement volumetric flowmeter, which combination is particularly effective in measuring mass flow rates of highly viscous fluids or mixtures of gaseous and fluid medium.

SUMMARY OF THE INVENTION

The primary object of the present invention is to provide a density meter employing one or two sections of a conduit vibrating at different natural frequencies, wherein the density of the fluid moving through the vibrating conduit is determined from a combination of the two different natural frequencies Another object is to provide a density meter employing one or two sections of a conduit under flexural vibrations, wherein the density of the fluid moving through the conduit is determined independent of the viscosity of the fluid.

A further object is to provide a density meter comprising a single section of a conduit under flexural vibrations in two orthogonal lateral directions at two different natural frequencies.

Yet another object is to provide a density meter comprising two sections of a conduit under flexural vibrations of two different natural frequencies, which two sections of the conduit are disposed in series.

Yet a further object is to provide a density meter comprising two sections of a conduit under flexural vibrations at two different natural frequencies, which two sections of the conduit are disposed in parallel arrangement.

Still another object is to provide a density meter including one or two sections of a conduit under continuously induced flexural vibrations at two different natural frequencies.

Still a further object is to provide a density meter including one or two sections of a conduit under intermittently induced flexural vibrations at two different natural frequencies.

These and other objects of the present invention !will become clear as the description thereof progresses.

BRIEF DESCRIPTION OF THE FIGURES

The present invention may be described with a great clarity and specificity by referring to the following figures :

FIG. 1 illustrates an embodiment of the dual frequency density meter of the present invention including two vibrating sections of a conduit disposed in series, wherein the conduit includes a 360 degree loop.

FIG. 2 illustrates a cross section of the first half of the looping conduit vibrating at a first natural frequency.

FIG. 3 illustrates a cross section of the second half of the looping conduit vibrating at a second natural frequency.

FIG. 4 illustrates an embodiment of the dual frequency density meter including two U-shaped vibrating sections of a conduit disposed in series.

FIG. 5 illustrates a cross section of the first U-shaped section of the conduit.

FIG. 6 illustrates a cross section of the second U-shaped section of the conduit.
meter FIG. 7 illustrates an embodiment of the dual frequency density including two straight vibrating sections of a conduit disposed in an U-shaped arrangement.

FIG. 8 illustrates an embodiment of the dual frequency density meter comprising a pair of angled vibrating sections of a conduit disposed in an U-shaped arrangement.

FIG. 9 illustrates an embodiment of the dual frequency density meter including a pair of U-shaped vibrating sections of a conduit disposed in a looping arrangement.

FIG. 10 illustrates an embodiment of the dual frequency density meter including an over-hanging vibrating section of a conduit.

FIG. 11 illustrates an embodiment of the dual frequency density meter including a pair of U-shaped vibrating conduits included in a 360 degree loop of a conduit.

FIG. 12 illustrates an embodiment of the dual frequency density meter including a single straight vibrating section of a conduit.

FIG. 13 illustrates a cross section of the straight vibrating section of the conduit included in the embodiment shown in FIG. 12.

FIG. 14 illustrates an embodiment of the dual frequency density meter comprising a single straight vibrating section of a conduit with one extremity including a flexible coupling.

FIG. 15 illustrates a cross section of the straight vibrating section of the conduit included in the embodiment shown in FIG. 14.

FIG. 16 illustrates another embodiment of the dual frequency density meter comprising a vibrating section of a conduit with one extremity including a flexible coupling.

FIG. 17 illustrates a further embodiment of the dual frequency density meter comprising a vibrating section of a conduit with one extremity including a flexible coupling.

FIG. 18 illustrates an embodiment of the dual frequency density meter comprising a straight vibrating section of a conduit with both extremities respectively including two flexible couplings and two orthogonal flexural motion restrainers.

Operating Principles of the Invention

Figure 19:
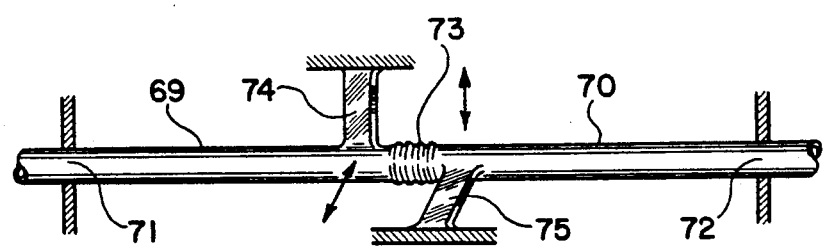
FIG. 19 illustrates an embodiment of the dual frequency density meter comprising a straight vibrating section of a conduit with a flexible coupling included at a midsection thereof and a pair of orthogonal flexural motion restrainers respectively disposed at two opposite sides of the flexible coupling.

Newton's second law of motion governing the natural flexural vibration straight conduit disposed on the x-axis of a Cartesian coordinate system can be written in the following form:

$$EI \frac{\partial^4 y}{\partial x^4} + (A\mu_0 + B\mu)D \frac{\partial y}{\partial t} + \left( m + \frac{\pi}{4} D^2 \rho \right) \frac{\partial^2 y}{\partial t^2} = 0, \quad (1)$$

where E is Young's modulus of the material making up the wall of the conduit, I is the moment of intertia of the cross section of the conduit, y is the lateral deflection of the conduit. A and B are constants, $\mu_0$ and $\mu$ are the viscosity of the fluids occupying the exterior and interior spaces of the conduit, D is the internal diameter of the conduit, t is the time, m is the linear density of the conduit itself and $\rho$ is the density of the fluid occupying the interior space of the conduit. It is readily found that equation (1) a solution of the following form:

$$y(x,t) = X(x)\exp\left\{ \left[ -\frac{D}{2} \frac{A\mu_0 + B\mu}{m + \frac{\pi}{4} D^2\rho} \pm i\sqrt{\frac{EI\lambda}{m + \frac{\pi}{4} D^2\rho} - \left( \frac{D}{2} \frac{A\mu_0 + B\mu}{m + \frac{\pi}{4} D^2\rho} \right)^2} \right] t \right\}, \quad (2)$$

where X(x) stands for a function of x, exp. stands for the exponential function and $\lambda$ is a characteristic value to be determined from the boundary conditions of the conduit. Substitution of equation (2) into (1) yields the equation $$\frac{d^4 X}{dx^4} - \lambda X = 0. \quad (3)$$

The characteristic value $\lambda$ is determined by applying the boundary condition the conduit to the solution of equation (3). For example, the numerical value of ($\lambda^{\frac{1}{4}} L$), where L is the length of the vibrating section of the conduit, for the primary mode of vibration of the conduit determined theoretically is equal to 4.730 for a conduit with both ends clamped or both ends free and 1.875 for a conduit with one end fixed and one end free.

According to the solution given by equation (2). the natural frequency f of the flexural vibration of the conduit is given by equation $$f = \frac{1}{2\pi} \sqrt{\frac{EI\lambda}{m + \frac{\pi}{4} D^2\rho} - \left( \frac{D}{2} \frac{A\mu_0 + B\mu}{m + \frac{\pi}{4} D^2\rho} \right)^2}. \quad (4)$$

Equation (4) can be simplified for a vibrating conduit in air or vacuum wherein $\mu_0$ is negligibly small as follows, $$f = \frac{1}{2\pi} \sqrt{\frac{EI\lambda}{m + \frac{\pi}{4} D^2\rho} - \left( \frac{B\mu D}{2m + \frac{\pi}{2} D^2\rho} \right)^2}. \quad (5)$$

According to equation (4) or (5), the natural frequency of the flexural vibration of a conduit is a function of the density and viscosity of fluid contained in the conduit. If a single section of a conduit is under two flexural vibrations in two orthogonal lateral directions, or two sections of a conduit are two flexural vibrations at two different natural frequencies, the natural of the two flexural vibrations of a vibrating conduit in air or are given by equations $$\pi^2 (f_1)^2 = \frac{EI_1\lambda_1}{4m + \pi D^2\rho} - \left( \frac{B\mu D}{4m + \pi D^2\rho} \right)^2, \quad (6)$$

and $$\pi^2 (f_2)^2 = \frac{EI_2\lambda_2}{4m + \pi D^2\rho} - \left( \frac{B\mu D}{4m + \pi D^2\rho} \right)^2. \quad (7)$$

By subtracting equation (7) from equation (6), the term including the fluid is eliminated and a relationship relating the fluid density to the two natural frequencies of the flexural vibration is obtained, $$\rho = \frac{1}{\pi^3 D^2} \frac{E(I_1\lambda_1 - I_2\lambda_2)}{(f_1)^2 - (f_2)^2} - \frac{4m}{\pi D^2}. \quad (8)$$

Equation (8) is a theoretical equation, which may be written in more general form as follows :

$$\rho = \frac{G}{(f_1)^2 - (f_2)^2} - H, \quad (9)$$

where G and H are constants intrinsic to the solid mechanics property of the vibrating conduit, which are independent of the property of the fluid contained in the conduit. The constants G and H are determined empirically by calibrating the dual frequency vibrating tube density meter of the present invention by using two different sample fluids of known density. Equation (9) is derived based on theory of mechanics. In real world, theory may deviate from true reality up to certain extent. In place of equation (9), one may use an empirical counterpart of the form $\pi = F(f_1, f_2)$ determined by experiments instead of the theory. It has now been proven that the density of a fluid contained in a conduit can be determined from two different natural frequencies of flexural vibrations of a single vibrating section of a conduit experiencing two flexural vibrations in two orthogonal lateral directions or from two different natural frequencies of flexural vibrations of two different sections of a conduit, as shown by equation (9) that is the basis of the operating principles of the present invention.

DESCRIPTION OF THE ILLUSTRATED EMBODIMENTS

In FIG. 1 there is illustrated a perspective view of an embodiment of dual frequency vibrating conduit density meter, that comprises a conduit 1 including a 360 degree loop 2 intermediate two anchored port legs 3 and 4 wherein the two generally straight sections 5 and 6 respectively included in the two halves of the conduit 1, extend towards each other from the anchored extremities thereof and are connected to one another by the 360 degree loop section 2 of the conduit. The midsection 7 of the looped conduit 1 is rigidly anchored to the frame 8. An electromagnet 9 induces flexural vibrations on the two of the conduit. A pair of motion sensors 10 and 11 respectively detect flexural vibrations of the two halves of the conduit 1. As shown in FIGS. 2 and 3, the two halves of the conduit 1 have different flexural stiffness and, consequently, vibrate at two different natural frequencies. It should be mentioned that the two generally straight sections 5 and 6 of the conduit 1 may be disposed in an arrangement parallel to one another and extending respectively from port legs in an overhanging relationship wherein the two generally straight sections of the conduit are now connected to one another by a looped section of the conduit of loop angle generally equal to 540 degrees. Of course, the two generally straight sections 5 and 6 of the conduit may be disposed in other arrangements wherein the angle therebetween is greater than zero degrees (in-line) and less than 180 degrees (parallel), and the two generally straight sections are connected to one another by a looped section of the conduit of loop angle in the range of 360 to 540 plus degrees.

In FIG. 2 there is illustrated a cross section of the first half of the looped conduit 1 taken along plane 2—2 as shown in FIG. 1.

In FIG. 3 there is illustrated a cross section of the second half of the looped conduit 1 taken along plane 3—3 as shown in FIG. 1. It is noticed that the two halves of the looped conduit 1 have the same internal diameter and different external diameters. As a consequence, the two halves of the looped conduit 1 vibrate laterally at two different natural frequencies. There are many other arrangements for making the two laterally vibrating sections of the conduit vibrate at two different natural frequencies, which may involve the two different conduit cross sections of the two vibrating sections having different moments of inertia in the cross sections as exemplified by the illustrative embodiments shown in FIGS. 5 and 6, 13 and 15 or may include external spring bias as exemplified by the illustrative embodiments shown in FIGS. 16, 17, 18, 19, 21 and 22. Of course, as suggested by equations (3) and (4), two different natural frequencies of the two laterally vibrating sections of the conduit can be obtained by employing different boundary conditions (rigidity or stiffness in the anchoring of the extremities of the vibrating sections of the conduit), while employing the identical cross section of the conduit for both vibrating sections of the conduit.

The dual frequency vibrating conduit density meter of the present invention exemplified by the embodiment shown in FIGS. 1, 2 and 3 may operate in two different modes. In the first mode of operation, the electromagnetic vibrator 9 imposes flexural vibrations on the two halves of the conduit in an intermittent manner by applying a mechanical impulse thereto at a regular time interval, wherein the intermittently induced flexural vibrations experience an attenuation in time before the next impulse is applied by the electromagnetic vibrator. An electronic data precessor detects the two different natural frequencies of the flexural vibrations from the signals supplied by the motion detectors 10 and 11. The fluid density is determined by carrying out the algorithm defined by equation (9) or empirical counterpart thereof, which algorithm is carried by the electronic data processor that is not shown in the illustrative embodiment. In the second mode of operation, the electromagnet vibrator 9 applies a vibratory force in a frequency sweep mode, that is continuously repeated in time. The electronic data processor determines the natural frequencies signals supplied by the motion detectors 10 and 11 by detecting the frequencies corresponding to the maximum amplitudes in the signals generated in a frequency sweep mode. Once two different natural frequencies of the two vibrating sections are detected, they are substituted into equation (9) or empirical counterpart thereof to determine the fluid density, which calculation is performed by an electronic data Processor. In order completely eliminate the effect of the ambient air resistance on the flexural vibrations of the conduit that is a source of error in determining the fluid density, the vibrating sections of the conduit may be sealed in an evacuated container. It should be mentioned that the two vibrating sections of the conduit may have different inner diameters and/or different outer diameters, if specific operating conditions demand such an arrangement, in which case B and D in equations (6) and (7) are no longer the common constants and, yet, these two equations can be readily solved for the fluid density. All of the different embodiments of the dual frequency vibrating conduit density meter shown as illustrative embodiment operate on essentially the same principles as those described in conjunction with FIGS. 1, 2 and 3 apart from the specific arrangements designed to obtain the two different natural frequencies of the flexural vibrations.

In FIG. 4 there is illustrated an embodiment of the dual frequency vibrating conduit density meter comprising a pair of U-shaped sections 12 and 13 of the conduit disposed in series, wherein each of the two U-shaped conduits includes an electromagnetic vibrator 14 and a motion detector 15, which may be two separate and independent elements or an integral element performing the two functions. The two U-shaped sections 12 and 13 of the conduit have two different natural frequencies of flexural vibrations, wherein the vibratory motions generally perpendicular to the plane including the U-shaped sections of the conduit, as the two U-shaped sections of the conduit have different flexural stiffness.

In FIG. 5 there is illustrated a cross section of the first U-shaped section 12 of the conduit taken along plane 5—5 as shown in FIG. 4.

In FIG. 6 there is illustrated a cross section of the second U-shaped section 13 of the conduit taken along plane 6—6 as shown in FIG. 4. As a design means providing two different natural frequencies of flexural vibrations, the two side portions of the wall of the second U-shaped section of the conduit are shaved off in order to reduce the moment of inertia of the cross section about a plane including the U-shaped section of the conduit.

In FIG. 7 there is illustrated an embodiment of the dual frequency vibrating conduit density meter comprising a U-shaped conduit 16 that includes a pair of generally parallel straight vibrating sections 17 and 18 disposed in series. Each of the two straight vibrating sections 17 and 18 of the conduit includes a motion detector 19, while a common electromagnetic vibrator 20 induces flexural vibrations on both vibrating sections 17 and 18 in an intermittent or continuous manner as described in conjunction with FIGS. 1, 2 and 3. Of course, the two generally straight vibrating sections 17 and 18 must have different natural frequencies of flexural vibration, which condition is realized by employing different flexural stiffnesses of the conduits or different boundary conditions for the two vibrating sections 17 and 18. It is evident that the two generally straight vibrating sections of the conduit may be disposed in an in-line arrangement similar to the embodiment shown in FIG. 20 instead of the parallel arrangement in the U-shaped conduit shown in FIG. 7.

In FIG. 8 there is illustrated an embodiment of the dual frequency vibrating conduit density meter including a pair of generally straight vibrating sections 21 and 22 of a conduit respectively extending from the two port legs in a parallel and over-hanging arrangement, wherein the angled extremities 23 and 24 thereof are connected to a rigid section 25 of conduit by a pair of flexible couplings 26 and 27. The extremities of the vibrating sections 21 and 22 adjacent to the two port legs as well as the rigid section 25 are anchored rigidly to a frame. The two vibrating sections 21 and 22 have different flexural stiffness and, consequently, have two different natural frequencies of flexural vibration, from which the density of the fluid is determined by the method described in conjunction with equation (9). As another design implementation, the pair of flexible couplings 26 and 27 may be installed respectively at the roots of the two straight sections of the U-shaped conduit adjacent to the two port legs, respectively.

In FIG. 9 there is illustrated an embodiment of the dual frequency vibrating conduit density meter comprising a pair of U-shaped vibrating sections 28 and 29 of a conduit arranged in series in terms of fluid flow and side-by-side in terms of geometrical arrangement, which U-shaped vibrating sections are included in a generally oblong 540 degree loop of the conduit disposed intermediate two port legs 30 and 31. The two U-shaped vibrating sections have different natural frequencies of flexural vibrations. For the sake of simplicitycity of the illustration, the electromagnetic vibrator and the motion sensors are not shown in FIG. 9 and other figures which follow.

In FIG. 10 there is illustrated an embodiment of the dual frequency vibrating conduit density meter including an over-hanging vibrating section 32 of the conduit extending from the two port legs 33 and 34, which vibrating section 32 includes a pair of two straight sections 35 and 36 respectively in a side-by-side arrangement, which vibrating sections are fused into a single vibrating cantilever beam and connected to one another by generally 360 degree loop section 37 of the conduit. This over-hanging section 32 of the conduit vibrates laterally in two orthogonal directions wherein the first direction of the flexural vibration is parallel to the plane including both straight sections 35 and 36 of the conduit and the second direction is perpendicular to the first direction. It is clear that the two flexural vibrations of the over-hanging vibrating section 32 of the conduit in the two different directions have different natural frequencies because of different flexural stiffnesses thereof in the two directions. It should be mentioned that the flexural vibrations of the over-hanging section 32 of the conduit in the two different directions may be induced by two different electromagnetic vibrators respectively applying mechanical impulses or vibratory forces in the two different directions or a single electromagnetic vibrator applying mechanical impulse or vibratory force in a direction intermediate the two directions of the flexural vibrations. Of course, it is generally preferred to have two motion detectors respectively detecting the flexural vibrations in the two directions, even though a single motion detector disposed on a plane 45 degrees to the two planes wherein the two flexural vibrations take place can detect both flexural vibrations. It is evident that the straight portion of the over-hanging vibrating section 32 of the conduit can be a single elongated member including two parallel flow passages therein instead of the two sections 35 and 36 of the conduit tied or connected to one another.

In FIG. 11 there is illustrated an embodiment of the dual frequency vibrating conduit density meter including a pair of U-shaped vibrating sections 38 and 39 of conduit included in a generally 360 degree oblong loop 40 of conduit disposed intermediate two port legs 41 and 42, which U-shaped vibrating sections 38 and 39 have two different natural frequencies of flexural vibration In FIG. 12 there is illustrated am embodiment of the dual frequency vibrating conduit density meter comprising a single straight vibrating section 43 of a conduit with two fixed ends respectively connected to two port legs 44 and 45. The cross section of the straight vibrating section 43 of the conduit has two different moments of inertia about two orthogonal planes parallel to the central axis of the conduit and, consequently, two flexural vibrations of the straight vibrating section 43 in two orthogonal lateral directions have two different natural frequencies.

In FIG. 13 there is illustrated a cross section of the straight vibrating section 43 of the conduit taken along plane 13—13 as shown in FIG. 12, which cross section shows the flow passage with a circular cross section and the conduit with an oblong circular cross section. Of course, in place of the conduit having an oblong circular cross section, a conduit with a circular cross section having two sides shaved off as shown in FIG. 15 or other design such as a circular conduit with a reinforcing fin welded along the conduit may be employed, as almost any nonaxisymmetric cross section of the conduit provides two flexural vibrations in two orthogonal lateral directions occurring at two different natural frequencies. The two flexural vibrations in the two orthogolateral lateral directions may be induced by two electromagnetic vibrators respectively installed on two orthogonal planes parallel to the central axis of the conduit or by a single electromagnetic vibrator 46 installed on a plane generally 45 degrees to both of the two planes whereon the two flexural vibrations respectively take place.

In FIG. 14 there is illustrated another embodiment of the dual frequency vibrating conduit density meter comprising a single straight vibrating section 47 of a conduit disposed intermediate two port legs 48 and 49. One extremity of the vibrating section 47 is fixedly connected to the first port leg 48 rigidly anchored to a frame and the other extremity is connected to the second port leg 49 rigidly anchored to the frame in a laterally flexible arrangement by means of the flexible coupling 50. As the two diagonally opposite sides of the external surface of the vibrating section 47 are shaved off, the two flexural vibrations in the two orthogonal lateral directions have two different natural frequencies.

In FIG. 15 there is illustrated a cross section of the vibrating section 47 of the conduit taken along plane 15—15 as shown in FIG. 14. A conduit with two shaved off sides as shown in the particular illustrated embodiment.

In FIG. 16 there is illustrated a further embodiment of the dual frequency vibrating conduit density meter having essentially the same construction as the embodiment shown in FIG. 14 with one exception. The straight vibrating section 52 of a conduit has an angled extremity 53 connected to an exit port leg 54 by a flexible coupling 55, which angled extremity is supported by a compressive coil spring 56 disposed laterally on a plane including the angled extremity 53 of the vibrating section 52 of the conduit and the exit port leg 54. The vibrating section 52 of the conduit with a circular or noncircular cross section vibrates in two orthogonal lateral directions respectively perpendicular and parallel to the plane including the central axis of the flexible coupling 55 and the coil spring 56 at two different natural frequencies.

In FIG. 17 there is illustrated yet another embodiment of the dual frequency vibrating conduit density meter having essentially the same construction as the embodiment shown in FIG. 16 with a few exceptions. One extremity of the vibrating section 57 of a conduit is rigidly anchored to a frame, while the other extremity with a Tee coupling 58 is connected to a Y-shaped port leg 59 by a pair of flexible couplings 60 and 61. The straight vibrating section 57 of the conduit vibrate in two orthogonal lateral directions respectively perpendicular and parallel to a plane including the central axis of the flexible couplings 60 and 61 at two different natural frequencies.

In FIG. 18 there is illustrated an embodiment of the dual frequency vibrating conduit density meter comprising a single straight vibrating section 62 of a conduit with two extremities respectively connected to two port legs 63 and 64 by a pair of flexible couplings 65 and 66, respectively. One extremit the vibrating section 62 of the conduit is supported by a first leaf spring disposed on a first plane parallel to the central axis of the conduit and anchored to a frame, while the other extremity of the vibrating section 62 of the conduit is supported by a second leaf spring 68 disposed on a second plane parallel to the central axis of the conduit and perpendicular to the first plane which second leaf spring 68 is also anchored to the frame. One extremity of the vibrating section 62 of the conduit supported by the leaf spring 67 vibrates in a first lateral direction perpendicular to the leaf spring 67 at a first natural frequency, while the other extremity supported by the leaf spring 68 vibrates in a second direction perpendicular to the leaf spring 68 at a second natural frequency.

In FIG. 19 there is illustrated an embodiment of the dual frequency vibrating conduit density meter comprising a pair of vibrating sections 69 and 70 of a conduit respectively extending from two port legs 71 and 72 towards each other in line and connected to one another by a flexible coupling 73. One extremity of the vibrating section 69 of the conduit adjacent to the flexiflexible flexible coupling 73 is reinforced by a first leaf spring 74 disposed on a first plane parallel to the central axis of the conduit and anchored to a frame, which extremity vibrates in a first lateral direction perpendicular to the leaf spring 74 at a first natural frequency, while one extremity of the vibrating section 70 of the conduit adjacent to the flexible coupling 73 is reinforced by a second leaf spring 75 disposed on a second plane parallel to the central axis of the conduit and perpendicular to the first plane and anchored to the frame, which extremity vibrates in a second lateral direction perpendicular to the leaf spring 75 at a second natural frequency.

Figure 20:
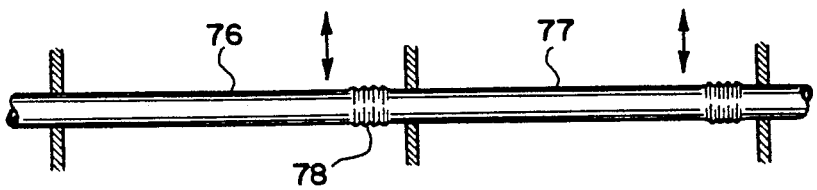
FIG. 20 illustrates an embodiment of the dual frequency density meter including two straight vibrating sections of a conduit respectively including two flexible couplings, which vibrating sections are disposed in series.

In FIG. 20 there is illustrated an embodiment of the dual frequency vibrating conduit density meter comprising a pair of straight vibrating sections 76 and 77 of the conduit disposed in series, wherein one extremity of each of the two vibrating sections 76 and 77 includes a flexible coupling 78, while the other extremity is rigidly anchored to a frame. The two vibrating sections 76 and 77 of the conduit vibrate at two different natural frequencies. It should be mentioned that the embodiment shown in FIG. 20 works equally well without the pair of flexible couplings respectively included in the two vibrating sections 76 and 77 of the conduit.

Figure 21:
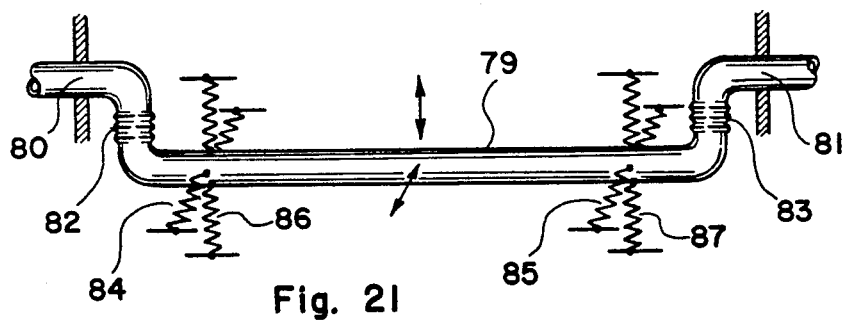
FIG. 21 illustrates an embodiment of the dual frequency density meter including a vibrating section of a conduit supported by two orthogonal bias springs.

In FIG. 21 there is illustrated an embodiment of the dual frequency vibrating conduit density meter comprising a generally straight vibrating section 79 of a conduit with two angled extremities respectively connected to two port legs 80 and 81 by a pair of flexible couplings 82 and 83, respectively. The two extremities of the vibrating section 79 of the conduit are reinforced forced by a first set of coil springs 84, 85, etc. disposed on a first plane parallel to the central axis of the conduit and by a second set of coil springs 86, 87 etc. disposed on a second plane parallel to the central axis of the conduit and perpendicular to the first plane. The vibrating section 79 of the conduit vibrates transversely in two lateral directions respectively perpendicular to the first and second planes at two different natural frequencies. In this embodiment, the vibrating section 79 of the conduit experiences little bending deflection, as the deflections allowing the transverse vibrations are provided by the flexible couplings 82 and 83.

Figure 22:
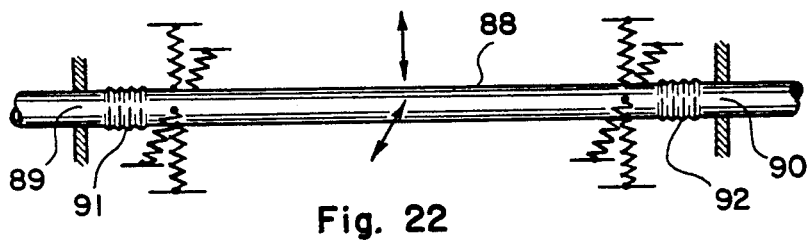
FIG. 22 illustrates another embodiment of the dual frequency density including a straight vibrating section of a conduit supported by two orthogonal bias springs.

In FIG. 22 there is illustrated an embodiment of the dual frequency vibrating conduit density meter having essentially the same construction as the embodiment shown in FIG. 21 with the only exception being that the vibrating section 88 of a conduit is connected to two port legs 89 and 90 by a pair of flexible couplings 91 and 92 in an in-line arrangement instead of angled connections.

Figure 23:
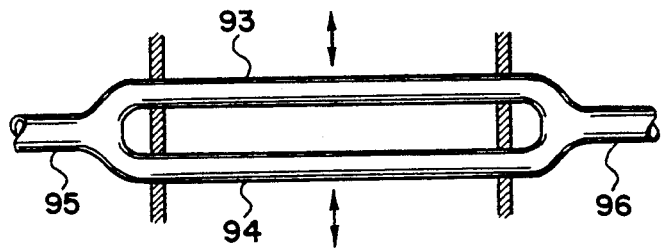
FIG. 23 illustrates an embodiment of the dual frequency density meter including a pair of straight vibrating sections of a conduit disposed in a parallel arrangement.

In FIG. 23 there is illustrated an embodiment of the dual frequency vibrating conduit density meter comprising a pair of vibrating sections 93 and 94 of conduit disposed in a parallel arrangement and connected to two common port legs 95 and 96 at two opposite extremities. The two vibrating sections 93 and 94 vibrate at two different natural frequencies. In place of the solid conduit sections 93 and 94 employed in the particular illustrative embodiment, conduit sections including a flexible coupling at one extremity thereof may be employed in the construction of the embodiment shown in FIG. 23.

Figure 24:
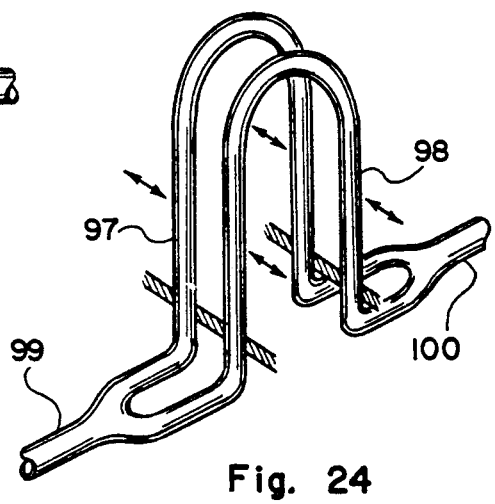
FIG. 24 illustrates an embodiment of the dual frequency density meter including a pair of U-shaped sections of a conduit disposed in a parallel arrangement.

In FIG. 24 there is illustrated an embodiment of the dual frequency vibrating conduit density meter including a pair of U-shaped vibrating sections and 98 of conduit disposed in a parallel arrangement and connected to two common port legs 99 and 100, which U-shaped vibrating sections 97 and 98 of the conduit vibrate at two different natural frequencies.

It should be mentioned that a dual frequency density meter employing one or two solid vibrating conduit sections vibrating at high natural frequencies such as the embodiments shown in FIGS. 1, 4, 7, 9, 10, 11, 12, 23 and 24 is the best choice for measuring density of a fluid that is not subjected to cavitation or effervescence promoted by the high frequency lateral vibrations of the vibrating sections of the conduit. If the fluid through the density meter is at a state wherein cavitation or effervescence take place, a dual frequency density meter employing one or two vibrating sections vibrating at low natural frequencies such as the embodiments shown in FIGS. 8, 14, 16, 17, 18, 19, 20, 21, and 22 should be employed in order to prevent the cavitation or effervescence promoted by the lateral vibration of the flow passage, which can create a serious error in measuring the fluid density. It is generally recommended to seal the vibrating conduit sections of the dual frequency density meter within an evacuated container wherein only the inlet and outlet flanges are disposed exterior to the evacuated container in order to eliminate the clamping effect of the ambient air surrending the vibrating conduit sections, that can introduce an error in the measurement of the fluid density.

While the principles of the present invention have now been made clear by the illustration embodiments, there will be many obvious modifications of the structures, arrangements, proportions, elements and materials, which are particularly adapted to the specific working environments and operating conditions in the practice of the invention without departing from those principles. It is not desired to limit the inventions to the particular illustrative embodiments shown and described and, accordingly, all suitable modifications and equivalents may be resorted to falling within the scope of the inventions as defined by the claims which follow.

What is claimed is:

1. A method for measuring density of media comprising in combination:
   (a) creating two different natural frequencies of flexural vibration of conduit containing the media by laterally vibrating at least one conduit providing at least one flow passage;
   (b) measuring the two natural frequencies of flexural vibration; and
   (c) determining density of the media as a function of a ratio of a parameter to a differential combination of the squares of the two natural frequencies of flexural vibration, wherein effect of viscosity of the media on the two natural frequencies of flexural vibration is eliminated in determining the media density as said function of the two natural frequencies of flexural vibration.

2. A method as set forth in claim 1 wherein the two natural frequencies of flexural vibration are obtained by laterally vibrating the conduit in two different lateral directions.

3. A method as set forth in claim 2 wherein the two natural frequencies are obtained by laterally vibrating the conduit in continuous mode.

4. A method as set forth in claim 2 wherein the two natural frequencies are obtained by laterally vibrating the conduit in intermittent mode.

5. A method as set forth in claim 2 wherein the two natural frequencies are obtained by laterally vibrating the conduit in frequency sweep mode, wherein natural frequency is determined from frequency corresponding to maximum amplitude of flexural vibration in frequency domain.

6. A method as set forth in claim 1 wherein the two natural frequencies of flexural vibration are obtained by laterally vibrating two different sections of conduit connected to one another in series, wherein the two sections of conduit respectively have the two different natural frequencies of flexural vibration.

7. A method as set forth in claim 6 wherein the two natural frequencies are obtained by laterally vibrating the two sections of conduit in continuous mode.

8. A method as set forth in claim 6 wherein the two natural frequencies are obtained by laterally vibrating the two sections of conduit in intermittent mode.

9. A method as set forth in claim 6 wherein the two natural frequencies are obtained by laterally vibrating the two sections of conduit in frequency sweep mode, wherein natural frequency is determined from frequency corresponding to maximum amplitude of flexural vibration in frequency domain.

10. A method as set forth in claim 1 wherein the two natural frequencies of flexural vibration are obtained by laterally vibrating two conduits providing two parallel flow passages, wherein the two conduits respectively have the two different natural frequencies of flexural vibration.

11. A method as set forth in claim 10 wherein the two natural frequencies are obtained by laterally vibrating the two conduits in continuous mode.

12. A method as set forth in claim 10 wherein the two natural frequencies are obtained by laterally vibrating the two conduits in intermittent mode.

13. A method as set forth in claim 10 wherein the two natural frequencies are obtained by laterally vibrating the two conduits in frequency sweep mode, wherein natural frequency is determined from frequency corresponding to maximum amplitude of flexural vibration in frequency domain.

* * * * *